(12) United States Patent
Mack et al.

(10) Patent No.: US 6,316,272 B1
(45) Date of Patent: Nov. 13, 2001

(54) METHODS OF DIAGNOSIS OF COLORECTAL CANCER AND METHODS OF SCREENING FOR COLORECTAL CANCER MODULATORS

(75) Inventors: David Mack; Kurt C. Gish, both of Menlo Park; Keith E. Wilson, Redwood City, all of CA (US)

(73) Assignee: EOS Biotechnology, Inc., South San Francisco, CA (US)

( * ) Notice: Subject to any disclaimer, the term of this patent is extended or adjusted under 35 U.S.C. 154(b) by 0 days.

(21) Appl. No.: 09/268,866

(22) Filed: Mar. 15, 1999

(51) Int. Cl.$^7$ ............... G01N 33/53; C12Q 1/68; C12P 21/06; C07K 16/00
(52) U.S. Cl. ............... 436/500; 435/6; 435/7.1; 435/69.1; 530/387.1
(58) Field of Search ............... 435/6, 7.1, 69.1; 424/1.49; 436/500; 530/387.1

(56) References Cited

U.S. PATENT DOCUMENTS

| 5,514,554 | 5/1996 | Bacus . |
| 6,066,778 | * 5/2000 | Ginsburg et al. ............... 800/2 |

FOREIGN PATENT DOCUMENTS

| 99/33869 | 7/1997 | (WO) . |
| 98/18945 | 5/1998 | (WO) . |
| 98/34118 | 8/1998 | (WO) . |
| 99/23230 | 5/1999 | (WO) . |
| 00/08210 | 2/2000 | (WO) . |

OTHER PUBLICATIONS

Payne et al., "Primary Structure, Functional Expression, and Chromosomal Localization of the Bumetanide–sensitive Na–K–Cl Cotransporter in Human Colon" The Journal of Biological Chemistry, 1995, vol. 270, No. 30, pp. 17977–17985.*

Pallela et al., "99mTc–Labeled Vasoactive Intestinal Peptide Receptor Agonist: Functional Studies" The Journal of Nuclear Medicine, 1999, vol. 40, No. 2, pp. 352–360.*

Yamamoto et al., "Clinical application of chimeric monoclonal antibody A7–NCS conjugate" Biotherapy, 1996, vol. 10, No. 3, pp. 365–367.*

King et al., "Expression, purification and characterization of a mouse–human chimeric antibody and chimeric Fab' fragment" Biochemical Journal, 1992, vol. 281, Pt. 2, pp. 317–323.*

Sequence Homology Search.*

"Molecular Biology of Colorectal Cancer," *Curr. Probl. Cancer*, 238–299 (Sep./Oct. 1997).

Liefers et al., "Micrometastases and Survival in Stage II Colorectal Cancer," *New England J. of Med.*, 339(4):223–228 (1998).

\* cited by examiner

*Primary Examiner*—John S. Brusca
*Assistant Examiner*—Young Kim
(74) *Attorney, Agent, or Firm*—Flehr Hohbach Test Albritton & Herbert LLP

(57) ABSTRACT

Described herein are methods that can be used for diagnosis and prognosis of colorectal cancer. Also described herein are methods that can be used to screen candidate bioactive agents for the ability to modulate colorectal cancer. Additionally, molecular targets (genes and their products) for therapeutic intervention in colorectal and other cancers are described.

15 Claims, No Drawings

METHODS OF DIAGNOSIS OF COLORECTAL CANCER AND METHODS OF SCREENING FOR COLORECTAL CANCER MODULATORS

FIELD OF THE INVENTION

The invention relates to the identification of expression profiles and the nucleic acids involved in colorectal cancer, and to the use of such expression profiles and nucleic acids in diagnosis and prognosis of colorectal cancer. The invention further relates to methods for identifying candidate agents which modulate colorectal cancer.

BACKGROUND OF THE INVENTION

Colorectal cancer is a significant cancer in Western populations. It develops as the result of a pathologic transformation of normal colon epithelium to an invasive cancer. There have been a number of recently characterized genetic alterations that have been implicated in colorectal cancer, including mutations in two classes of genes, tumor-suppressor genes and proto-oncogenes, with recent work suggesting that mutations in DNA repair genes may also be involved in tumorigenesis.

For example, inactivating mutations of both alleles of the adenomatous polyposis coli (APC) gene, a tumor suppressor gene, appears to be one of the earliest events in colorectal cancer, and may even be the initiating event. Other genes implicated in colorectal cancer include the MCC gene, the p53 gene, the DCC (deleted in colorectal carcinoma) gene and other chromosome 18q genes, and genes in the TGF-β signalling pathway. For a review, see Molecular Biology of Colorectal Cancer, pp238–299, in Curr. Probi. Cancer, September/October 1997.

Imaging of colorectal cancer for diagnosis has been problematic and limited. In addition, dissemination of tumor cells (metastases) to locoregional lymph nodes is an important prognostic factor; five year survival rates drop from 80 percent in patients with no lymph node metastases to 45 to 50 percent in those patients who do have lymph node metastases. A recent report showed that micrometastases can be detected from lymph nodes using reverse transcriptase-PCR methods based on the presence of mRNA for carcinoembryonic antigen, which has previously been shown to be present in the vast majority of colorectal cancers but not in normal tissues. Liefers et al., New England J. of Med. 339(4):223 (1998).

Thus, methods that can be used for diagnosis and prognosis of colorectal cancer would be desirable.

Accordingly, it is an object of the invention to provide methods that can be used in diagnosis and prognosis of colorectal cancer. It is a further object to provide methods that can be used to screen candidate bioactive agents for the ability to modulate colorectal cancer. Additionally, it is an object to provide molecular targets for therapeutic intervention in colorectal and other cancers.

SUMMARY OF THE INVENTION

In accordance with the objects outlined above, the present invention provides novel methods for diagnosis and prognosis evaluation for colorectal cancer (CRC), as well as methods for screening for compositions which modulate CRC. In one aspect, a method of screening drug candidates comprises providing a cell that expresses an expression profile gene selected from the group consisting of the expression profile genes set forth in Tables 1, 2, 3, 4, 5, 6 and 7. The method further includes adding a drug candidate to said cell and determining the effect of said drug candidate on the expression of said expression profile gene.

In one embodiment, the method of screening drug candidates includes comparing the level of expression in the absence of said drug candidate to the level of expression in the presence of said drug candidate, wherein the concentration of said drug candidate can vary when present, and wherein said comparison can occur after addition or removal of the drug candidate. In a preferred embodiment, the cell expresses at least two expression profile genes. The profile genes may show an increase or decrease.

Also provided herein is a method of screening for a bioactive agent capable of binding to a colorectal cancer modulator protein (CCMP), said method comprising combining said CCMP and a candidate bioactive agent, and determining the binding of said candidate agent to said CCMP. Preferably the CCMP is a product encoded by a gene set forth in Tables 1–7.

Further provided herein is a method for screening for a bioactive agent capable of modulating the activity of a CCMP, said method comprising combining said CCMP and a candidate bioactive agent, and determining the effect of said candidate agent on the bioactivity of said CCMP. Preferably the CCMP is a product encoded by a gene set forth in Tables 1–7.

Additionally, provided herein is a method of evaluating the effect of a candidate colorectal cancer drug comprising administering said drug to a patient, removing a cell sample from said patient; and determining the expression profile of said cell. This method may further comprise comparing said expression profile to an expression profile of a healthy individual. In a preferred embodiment, said expression profile includes at least two genes selected from the group consisting of those set forth in Tables 1–7.

Moreover, provided herein is a biochip comprising a nucleic acid segment selected from the group consisting of the sequences set forth in Tables 1–7, wherein said biochip comprises fewer than 1000 nucleic acid probes. Preferable at least two nucleic acid segments are included.

In another aspect, a method of cloning a full length gene comprising using a nucleic acid segment selected from the group consisting of the sequences set forth in Tables 1–7 to clone the full length gene.

Furthermore, a method of diagnosing colorectal cancer is provided. Said method comprises determining the expression of a gene selected from the group consisting of set forth in Tables 1–7 in a first tissue type of a first individual; and comparing said distribution to the expression of said gene from a second normal tissue type from said first individual or a second unaffected individual. A difference in said expression indicates that the first individual has colorectal cancer.

Other aspects of the invention will become apparent to the skilled artisan by the following description of the invention.

Table 1 provides the Accession numbers for genes, including expression sequence tags, (incorporated in their entirety here and throughout the application where Accession numbers are provided), upregulated in tumor tissue compared to normal colon tissue. These include Accession number U30246 (SEQ ID No. 1).

Table 2 provides the Accession numbers for genes, including expression sequence tags, upregulated in tumor tissue compared to normal colon tissue.

Table 3 provides the Accession numbers for genes, including expression sequence tags, upregulated in tumor tissue compared to normal colon tissue.

Table 4 provides the Accession numbers for genes, including expression sequence tags, upregulated in tumor tissue compared to normal colon tissue.

Table 5 provides the Accession numbers for genes, including expression sequence tags, downregulated in tumor tissue compared to normal colon tissue.

Table 6 provides the Accession numbers for genes, including expression sequence tags, downregulated in tumor tissue compared to normal colon tissue.

Table 7 provides the Accession numbers for genes, including expression sequence tags, downregulated in tumor tissue compared to normal colon tissue.

DETAILED DESCRIPTION OF THE INVENTION

The present invention provides novel methods for diagnosis and prognosis evaluation for colorectal cancer (CRC), as well as methods for screening for compositions which modulate CRC. In one aspect, the expression levels of genes are determined in different patient samples for which either diagnosis or prognosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the cell. That is, normal tissue may be distinguished from CRC tissue, and within CRC tissue, different prognosis states (good or poor long term survival prospects, for example) may be determined. By comparing expression profiles of colon tissue in known different states, information regarding which genes are important (including both up- and down-regulation of genes) in each of these states is obtained. The identification of sequences that are differentially expressed in CRC versus normal colon tissue, as well as differential expression resulting in different prognostic outcomes, allows the use of this information in a number of ways. For example, the evaluation of a particular treatment regime may be evaluated: does a chemotherapeutic drug act to improve the long-term prognosis in a particular patient. Similarly, diagnosis may be done or confirmed by comparing patient samples with the known expression profiles. Furthermore, these gene expression profiles (or individual genes) allow screening of drug candidates with an eye to mimicking or altering a particular expression profile; for example, screening can be done for drugs that suppress the CRC expression profile or convert a poor prognosis profile to a better prognosis profile. This may be done by making biochips comprising sets of the important CRC genes, which can then be used in these screens. These methods can also be done on the protein basis; that is, protein expression levels of the CRC proteins can be evaluated for diagnostic purposes or to screen candidate agents. In addition, the CRC nucleic acid sequences can be administered for gene therapy purposes, including the administration of antisense nucleic acids, or the CRC proteins administered as therapeutic drugs.

Thus the present invention provides nucleic acid and protein sequences that are differentially expressed in colorectal cancer, CRC, herein termed "CRC sequences". As outlined below, CRC sequences include those that are up-regulated (i.e. expressed at a higher level) in CRC, as well as those that are down-regulated (i.e. expressed at a lower level) in CRC. In a preferred embodiment, the CRC sequences are from humans; however, as will be appreciated by those in the art, CRC sequences from other organisms may be useful in animal models of disease and drug evaluation; thus, other CRC sequences are provided, from vertebrates, including mammals, including rodents (rats, mice, hamsters, guinea pigs, etc.), primates, farm animals (including sheep, goats, pigs, cows, horses, etc). CRC sequences from other organisms may be obtained using the techniques outlined below.

CRC sequences can include both nucleic acid and amino acid sequences. In a preferred embodiment, the CRC sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a CRC protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the CRC sequences are nucleic acids. As will be appreciated by those in the art and is more fully outlined below, CRC sequences are useful in a variety of applications, including diagnostic applications, which will detect naturally occuring nucleic acids, as well as screening applications; for example, biochips comprising nucleic acid probes to the CRC sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res.

14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done for a variety of reasons, for example to increase the stability and half-life of such molecules in physiological environments or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occuring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathine hypoxathine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

A CRC sequence is initially identified by substantial nucleic acid and/or amino acid sequence homology to the CRC sequences outlined herein and identified by accession numbers in the tables. Such homology can be based upon the overall nucleic acid or amino acid sequence, and is generally determined as outlined below, using either homology programs or hybridization conditions.

In a preferred embodiment, CRC sequences are those that are up-regulated in CRC; that is, the expression of these genes is higher in colorectal carcinoma as compared to normal colon tissue. "Up-regulation" as used herein means at least about a two-fold change, preferably at least about a three fold change, with at least about five-fold or higher being preferred. Table 4 depicts 1815 genes, listed by accession number, that exhibit at least a 10 fold increase in expression levels as compared to normal colon tissue. All accession numbers herein are for the GenBank sequence database and the sequences of the accession numbers are hereby expressly incorporated by reference. GenBank is known in the art, see, e.g., Benson, D A, et al., Nucleic Acids Research 26:1–7 (1998) and http://www.ncbi.nlm.nih.gov/. In addition, these genes were found to be expressed in a limited amount or not at all in heart, brain, lung, liver, breast, kidney, prostate, small intestine and spleen. Table 3 depicts a preferred subset of the Table 1 genes, comprising 1144 genes. Table 2 depicts an additionally preferred subset comprising 194 genes. Table 1 depicts an particularly preferred subset comprising 51 genes.

In a preferred embodiment, CRC sequences are those that are down-regulated in CRC; that is, the expression of these genes is lower in colorectal carcinoma as compared to normal colon tissue. "Down-regulation" as used herein means at least about a two-fold change, preferably at least about a three fold change, with at least about five-fold or higher being preferred. Table 7 depicts 1923 genes, listed by accession number, that exhibit at least a 10 fold decrease in expression levels as compared to normal colon tissue. Table 6 depicts a preferred subset of the Table 4 genes, comprising 558 genes. Table 5 depicts an additionally preferred subset comprising 54 genes.

As used herein, a nucleic acid is a "CRC nucleic acid" if the overall homology of the nucleic acid sequence to the nucleic acid sequences of the accession numbers of the tables is preferably greater than about 75%, more preferably greater than about 80%, even more preferably greater than about 85% and most preferably greater than 90%. In some embodiments the homology will be as high as about 93 to 95 or 98%. Homology in this context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorith of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460–480 (1996); http:/lblast.wustl/edu/blastl REACRCE.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of the SEQ ID NOS. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the SEQ ID NOS., it is understood that the percentage of homology will be determined based on the number of homologous nucleosides in relation to the total number of nucleosides. Thus, for example, homology of sequences shorter than those of the sequences identified by accession numbers in the tables, as discussed below, will be determined using the number of amino acids in the shorter sequence.

In one embodiment, the nucleic acid homology is determined through hybridization studies. Thus, for example, nucleic acids which hybridize under high stringency to the nucleic acid sequences identified by accession numbers in the tables, or their complements, are considered a CRC sequence. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the CRC nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of the CRC genes can be obtained, using techniques well known in the art for cloning either longer sequences or the full length sequences; see Maniatis et al., and Ausubel, et al., supra, hereby expressly incorporated by reference.

Once the CRC nucleic acid is identified, it can be cloned and, if necessary, its constituent parts recombined to form the entire CRC nucleic acid. Once isolated from its natural source, e.g., contained within a plasmid or other vector or excised therefrom as a linear nucleic acid segment, the recombinant CRC nucleic acid can be further-used as a probe to identify and isolate other CRC nucleic acids, for example additional coding regions. It can also be used as a "precursor" nucleic acid to make modified or variant CRC nucleic acids and proteins.

The CRC nucleic acids of the present invention are used in several ways. In a first embodiment, nucleic acid probes to the CRC nucleic acids are made and attached to biochips to be used in screening and diagnostic methods, as outlined below, or for administration, for example for gene therapy and/or antisense applications. Alternatively, the CRC nucleic acids that include coding regions of CRC proteins can be put into expression vectors for the expression of CRC proteins, again either for screening purposes or for administration to a patient.

In a preferred embodiment, nucleic acid probes to CRC nucleic acids (both the nucleic acid sequences having the accession numbers outlined in the tables and/or the complements thereof) are made. The nucleic acid probes attached to the biochip are designed to be complementary to the CRC nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluorescese. A preferred substrate is described in copending application entitled Reusable Low Fluorescent Plastic Biochip filed Mar. 15, 1999, herein incorporated by reference in its entirety.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix Gene-Chip™ technology.

In a preferred embodiment, CRC nucleic acids encoding CRC proteins are used to make a variety of expression vectors to express CRC proteins which can then be used in screening assays, as described below. The expression vectors may be either self-replicating extrachromosomal vectors or vectors which integrate into a host genome.

Generally, these expression vectors include transcriptional and translational regulatory nucleic acid operably linked to the nucleic acid encoding the CRC protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the CRC protein; for example, transcriptional and translational regulatory nucleic acid sequences from Bacillus are preferably used to express the CRC protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The CRC proteins of the present invention are produced by culturing a host cell transformed with an expression vector containing nucleic acid encoding an CRC protein, under the appropriate conditions to induce or cause expression of the CRC protein. The conditions appropriate for CRC protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, HeLa cells, THPI cell line (a macrophage cell line) and human cells and cell lines.

In a preferred embodiment, the CRC proteins are expressed in mammalian cells. Mammalian expression systems are also known in the art, and include retroviral systems. A preferred expression vector system is a retroviral vector system such as is generally described in PCT/US97101019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, CRC proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the CRC protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors. Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, CRC proteins are produced in insect cells. Expression vectors for the transformation of insect cells, and in particular, baculovirus-based expression vectors, are well known in the art.

In a preferred embodiment, CRC protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The CRC protein may also be made as a fusion protein, using techniques well known in the art. Thus, for example, for the creation of monoclonal antibodies, if the desired epitope is small, the CRC protein may be fused to a carrier protein to form an immunogen. Alternatively, the CRC protein may be made as a fusion protein to increase expression, or for other reasons. For example, when the CRC protein is an CRC peptide, the nucleic acid encoding the peptide may be linked to other nucleic acid for expression purposes.

In one embodiment, the CRC nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

Accordingly, the present invention also provides CRC protein sequences. A CRC protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the CRC protein has homology to some protein in the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "Query Genetic Codes" is standard (1). The matrix is BLOSUM62; gap existence cost is 11, per residue gap cost is 1; and the lambda ratio is 0.85 default. This results in the generation of a putative protein sequence.

Also included within the definition of CRC proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

CRC proteins of the present invention may be shorter or longer than the wild type amino acid sequences. Thus, in a preferred embodiment, included within the definition of CRC proteins are portions or fragments of the wild type sequences. herein. In addition, as outlined above, the CRC nucleic acids of the invention may be used to obtain additional coding regions, and thus additional protein sequence, using techniques known in the art.

In a preferred embodiment, the CRC proteins are derivative or variant CRC proteins as compared to the wild-type sequence. That is, as outlined more fully below, the derivative CRC peptide will contain at least one amino acid substitution, deletion or insertion, with amino acid substitutions being particularly preferred. The amino acid substitution, insertion or deletion may occur at any residue within the CRC peptide.

Also included within the definition of CRC proteins of the present invention are amino acid sequence variants. These variants fall into one or more of three classes: substitutional, insertional or deletional variants. These variants ordinarily are prepared by site specific mutagenesis of nucleotides in the DNA encoding the CRC protein, using cassette or PCR mutagenesis or other techniques well known in the art, to produce DNA encoding the variant, and thereafter expressing the DNA in recombinant cell culture as outlined above. However, variant CRC protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the CRC protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed CRC variants screened for the optimal combination of desired activity. Techniques for making substitution mutations at predetermined sites in DNA having a known sequence are well known, for example, M13 primer mutagenesis and PCR mutagenesis. Screening of the mutants is done using assays of CRC protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the CRC protein are desired, substitutions are generally made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the CRC proteins as needed. Alternatively, the variant may be designed such that the biological activity of the CRC protein is altered. For example, glycosylation sites may be altered or removed.

Covalent modifications of CRC polypeptides are included within the scope of this invention. One type of covalent modification includes reacting targeted amino acid residues of an CRC polypeptide with an organic derivatizing agent that is capable of reacting with selected side chains or the N-or C-terminal residues of an CRC polypeptide. Derivatization with bifunctional agents is useful, for instance, for crosslinking CRC to a water-insoluble support matrix or surface for use in the method for purifying anti-CRC antibodies or screening assays, as is more fully described below. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the a-amino groups of lysine, arginine, and histidine side chains [T. E. Creighton, Proteins: Structure and Molecular Properties, W. H. Freeman & Co., San Francisco, pp. 79–86 (1983)], acetylation of the N-terminal amine, and amidation of any C-terminal carboxyl group.

Another type of covalent modification of the CRC polypeptide included within the scope of this invention comprises altering the native glycosylation pattern of the polypeptide. "Altering the native glycosylation pattern" is intended for purposes herein to mean deleting one or more carbohydrate moieties found in native sequence CRC polypeptide, and/or adding one or more glycosylation sites that are not present in the native sequence CRC polypeptide.

Addition of glycosylation sites to CRC polypeptides may be accomplished by altering the amino acid sequence thereof. The alteration may be made, for example, by the addition of, or substitution by, one or more serine or threonine residues to the native sequence CRC polypeptide (for O-linked glycosylation sites). The CRC amino acid sequence may optionally be altered through changes at the DNA level, particularly by mutating the DNA encoding the CRC polypeptide at preselected bases such that codons are generated that will translate into the desired amino acids.

Another means of increasing the number of carbohydrate moieties on the CRC polypeptide is by chemical or enzymatic coupling of glycosides to the polypeptide. Such methods are described in the art, e.g., in WO 87/05330 published 11 September 1987, and in Aplin and Wriston, CRC Crit. Rev. Biochem., pp. 259–306 (1981).

Removal of carbohydrate moieties present on the CRC polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of CRC comprises linking the CRC polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

CRC polypeptides of the present invention may also be modified in a way to form chimeric molecules comprising an CRC polypeptide fused to another, heterologous polypeptide or amino acid sequence. In one embodiment, such a chimeric molecule comprises a fusion of an CRC polypeptide with a tag polypeptide which provides an epitope to which an anti-tag antibody can selectively bind. The epitope tag is generally placed at the amino-or carboxyl-terminus of the CRC polypeptide. The presence of such epitope-tagged forms of an CRC polypeptide can be detected using an antibody against the tag polypeptide. Also, provision of the epitope tag enables the CRC polypeptide to be readily purified by affinity purification using an anti-tag antibody or another type of affinity matrix that binds to the epitope tag. In an alternative embodiment, the chimeric molecule may comprise a fusion of an CRC polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3C7, 6E10, G4, B7 and 9E10 antibodies thereto [Evan et al., Molecular and Cellular Biology, 5:3610–3616 (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

Also included with the definition of CRC protein are other CRC proteins of the CRC family, and CRC proteins from other organisms, which are cloned and expressed as outlined below. Thus, probe or degenerate polymerase chain reaction (PCR) primer sequences may be used to find other related CRC proteins from humans or other organisms. As will be appreciated by those in the art, particularly useful probe and/or PCR primer sequences include the unique areas of the CRC nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, CRC proteins can be made that are longer than those depicted in the accession numbers of the tables, for example, by the elucidation of additional sequences, the addition of epitope or purification tags, the addition of other fusion sequences, etc.

CRC proteins may also be identified as being encoded by CRC nucleic acids. Thus, CRC proteins are encoded by nucleic acids that will hybridize to the sequences of the sequence listings, or their complements, as outlined herein.

In a preferred embodiment, when the CRC protein is to be used to generate antibodies, the CRC protein must share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller CRC protein will be able to bind to the full length protein. In a preferred embodiment, the epitope is unique; 260 that is, antibodies generated to a unique epitope show little or no cross-reactivity. The term "antibody" includes antibody fragments, as are known in the art, including Fab, Fab$_2$, single chain antibodies (Fv for example), chimeric antibodies, etc., either produced by the modification of whole antibodies or those synthesized de novo using recombinant DNA technologies.

In a preferred embodiment, the antibodies to CRC are capable of reducing or eliminating the biological function of CRC, as is described below. That is, the addition of anti-CRC antibodies (either polyclonal or preferably monoclonal) to CRC (or cells containing CRC) may reduce or eliminate the CRC activity. Generally, at least a 25% decrease in activity is preferred, with at least about 50% being particularly preferred and about a 95–100% decrease being especially preferred.

The CRC antibodies of the invention specifically bind to CRC proteins. By "specifically bind" herein is meant that the antibodies bind to the protein with a binding constant in the range of at least $10^{-4}$–$10^{-6}$ M$^{-1}$, with a preferred range being $10^{-7}$–$10^{-9}$ M$^{-1}$.

In a preferred embodiment, the CRC protein is purified or isolated after expression. CRC proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the CRC protein may be purified using a standard anti-CRC antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the CRC protein. In some instances no purification will be necessary.

Once expressed and purified if necessary, the CRC proteins and nucleic acids are useful in a number of applications.

In a preferred embodiment, the CRC proteins, antibodies, nucleic acids, modified proteins and cells containing CRC sequences are used in diagnostic assays. This can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, Zlokarnik, et al., Science 279, 84–8 (1998), Heid, 1996 #69.

In one aspect, the expression levels of genes are determined for different cellular states in the CRC phenotype; that is, the expression levels of genes in normal colon tissue and in CRC tissue (and in some cases, for varying severities of CRC that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or CRC tissue.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, normal versus CRC tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the CRC protein and standard immunoassays (ELISAs,e tc.) or other techniques, including mass spectroscopy assays, 2D gel electrophoresis assays, etc. Thus, the proteins corresponding to CRC genes, i.e. those identified as being important in a CRC phenotype, can be evaluated in a CRC diagnostic test.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the CRC nucleic acid probes are attached to biochips as outlined herein for the detection and quantification of CRC sequences in a particular cell. The assays are further described below in the example.

It is understood that when comparing the fingerprints between an individual and a standard, the skilled artisan can make a diagnosis as well as a prognosis. It is further understood that the genes which indicate the diagnosis may differ from those which indicate the prognosis.

In a preferred embodiment, the CRC proteins, antibodies, nucleic acids, modified proteins and cells containing CRC sequences are used in prognosis assays. As above, gene expression profiles can be generated that correlate to CRC severity, in terms of long term prognosis. Again, this may be done on either a protein or gene level, with the use of genes being preferred. As above, the CRC probes are attached to biochips for the detection and quantification of CRC sequences in a tissue or patient. The assays proceed as outlined above for diagnosis.

In a preferred embodiment, the CRC proteins, antibodies, nucleic acids, modified proteins and cells containing the native or modified CRC proteins are used in screening assays. That is, the present invention provides novel methods for screening for compositions which modulate the CRC phenotype. As above, this can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokarnik, supra.

Having identified the differentially expressed genes herein, a variety of assays may be executed. In a preferred embodiment, assays may be run on an individual gene or protein level. That is, having identified a particular gene as up regulated in CRC, candidate bioactive agents may be screened to modulate this gene's response; preferably to down regulate the gene, although in some circumstances to up regulate the gene. "Modulation" thus includes both an increase and a decrease in gene expression. The preferred amount of modulation will depend on the original change of the gene expression in normal versus tumor tissue, with changes of at least 10%, preferably 50%, more preferably 100–300%, and in some embodiments 300–1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired.

As will be appreciated by those in the art, this may be done by evaluation at either the gene or the protein level; that is, the amount of gene expression may be monitored using nucleic acid probes and the quantification of gene expression levels, or, alternatively, the gene product itself can be monitored, for example through the use of antibodies to the CRC protein and standard immunoassays.

In a preferred embodiment, gene expression monitoring is done and a number of genes, i.e. an expression profile, is monitored simultaneously, although multiple protein expression monitoring can be done as well.

In this embodiment, the CRC nucleic acid probes are attached to biochips as outlined herein for the detection and quantification of CRC sequences in a particular cell. The assays are further described below.

Generally, in a preferred embodiment, a candidate bioactive agent is added to the cells prior to analysis. The term "candidate bioactive agent" or "drug candidate" or grammatical equivalents as used herein describes any molecule, e.g., protein, oligopeptide, small organic molecule, polysaccharide, polynucleotide, etc., to be tested for bioactive agents that are capable of directly or indirectly altering either the CRC phenotype or the expression of a CRC sequence, including both nucleic acid sequences and protein sequences. In preferred embodiments, the bioactive agents modulate the expression profiles, or expression profile nucleic acids or proteins provided herein. In a particularly preferred embodiment, the candidate agent suppresses a CRC phenotype, for example to a normal colon tissue fingerprint. Similarly, the candidate agent preferably suppresses a severe CRC phenotype. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occuring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occuring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

After the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occuring as needed, as will be appreciated by those in the art. For example, an in vitro transcription with labels covalently attached to the nucleosides is done. Generally, the nucleic acids are labeled with biotin-FITC or PE, or with cy3 or cy5.

In a preferred embodiment, the target sequence is labeled with, for example, a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay is run, the data is analyzed to determine the expression levels, and changes in expression levels as between states, of individual genes, forming a gene expression profile.

The screens are done to identify drugs or bioactive agents that modulate the CRC phenotype.

Specifically, there are several types of screens that can be run. A preferred embodiment is in the screening of candidate agents that can induce or suppress a particular expression profile, thus preferably generating the associated phenotype. That is, candidate agents that can mimic or produce an expression profile in CRC similar to the expression profile of normal colon tissue is expected to result in a suppression of the CRC phenotype. Thus, in this embodiment, mimicking an expression profile, or changing one profile to another, is the goal.

In a preferred embodiment, as for the diagnosis and prognosis applications, having identified the differentially expressed genes important in any one state, screens can be run to alter the expression of the genes individually. That is, screening for modulation of regulation of expression of a single gene can be done; that is, rather than try to mimic all or part of an expression profile, screening for regulation of individual genes can be done. Thus, for example, particularly in the case of target genes whose presence or absence is unique between two states, screening is done for modulators of the target gene expression.

In a preferred embodiment, screening is done to alter the biological function of the expression product of the differentially expressed gene. Again, having identified the importance of a gene in a particular state, screening for agents that bind and/or modulate the biological activity of the gene product can be run as is more fully outlined below.

Thus, screening of candidate agents that modulate the CRC phenotype either at the gene expression level or the protein level can be done.

Thus, in one embodiment, a candidate agent is administered to a population of CRC cells, that thus has an associated CRC expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, CRC tissue may be screened for agents that reduce or suppress the CRC phenotype. A change in at least one gene of the expression profile indicates that the agent has an effect on CRC activity. By defining such a signature for the CRC phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular differentially expressed gene as important in a particular state, screening of modulators of either the expression of the gene or the gene product itself can be done. The gene products of differentially expressed genes are sometimes referred to herein as "CRC proteins".

Thus, in a preferred embodiment, screening for modulators of expression of specific genes can be done. This will be done as outlined above, but in general the expression of only one or a few genes are evaluated.

In a preferred embodiment, screens are designed to first find candidate agents that can bind to differentially expressed proteins, and then these agents may be used in assays that evaluate the ability of the candidate agent to modulate differentially expressed activity. Thus, as will be appreciated by those in the art, there are a number of different assays which may be run; binding assays and activity assays.

In a preferred embodiment, binding assays are done. In general, purified or isolated gene product is used; that is, the gene products of one or more differentially expressed nucleic acids are made. In general, this is done as is known in the art. For example, antibodies are generated to the protein gene products, and standard immunoassays are run to determine the amount of protein present. Alternatively, cells comprising the CRC proteins can be used in the assays.

Thus, in a preferred embodiment, the methods comprise combining a CRC protein and a candidate bioactive agent, and determining the binding of the candidate agent to the CRC protein. Preferred embodiments utilize the human CRC protein, although other mammalian proteins may also be used, for example for the development of animal models of human disease. In some embodiments, as outlined herein, variant or derivative CRC proteins may be used.

Generally, in a preferred embodiment of the methods herein, the CRC protein or the candidate agent is non-diffusably bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the CRC protein is bound to the support, and a candidate bioactive agent is added to the assay. Alternatively, the candidate agent is bound to the support and the CRC protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the CRC protein may be done in a number of ways. In a preferred embodiment, the candidate bioactive agent is labelled, and binding determined directly. For example, this may be done by attaching all or a portion of the CRC protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. CRC), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present.

Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent.

Displacement of the competitor is an indication that the candidate bioactive agent is binding to the CRC protein and thus is capable of binding to, and potentially modulating, the activity of the CRC protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the CRC protein with a higher affinity. Thus, if the candidate bioactive agent is labeled, the presence of the label on the support, coupled with a lack of competitor binding, may indicate that the candidate agent is capable of binding to the CRC protein.

In a preferred embodiment, the methods comprise differential screening to identity bioactive agents that are capable of modulating the activitity of the CRC proteins. In this embodiment, the methods comprise combining an CRC protein and a competitor in a first sample. A second sample comprises a candidate bioactive agent, an CRC protein and a competitor. The binding of the competitor is determined for both samples, and a change, or difference in binding between the two samples indicates the presence of an agent capable of binding to the CRC protein and potentially modulating its activity. That is, if the binding of the competitor is different in the second sample relative to the first sample, the agent is capable of binding to the CRC protein.

Alternatively, a preferred embodiment utilizes differential screening to identify drug candidates that bind to the native CRC protein, but cannot bind to modified CRC proteins. The structure of the CRC protein may be modeled, and used in rational drug design to synthesize agents that interact with that site. Drug candidates that affect CRC bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of CRC may also be done. In a preferred embodiment, methods for screening for a bioactive agent capable of modulating the activity of CRC comprise the steps of adding a candidate bioactive agent to a sample of CRC, as above, and determining an alteration in the biological activity of CRC. "Modulating the activity of CRC" includes an increase in activity, a decrease in activity, or a change in the type or kind of activity present. Thus, in this embodiment, the candidate agent should both bind to CRC (although this may not be necessary), and alter its biological or biochemical activity as defined herein. The methods include both in vitro screening methods, as are generally outlined above, and in vivo screening of cells for alterations in the presence, distribution, activity or amount of CRC.

Thus, in this embodiment, the methods comprise combining an CRC sample and a candidate bioactive agent, and evaluating the effect on apoptosis. By "CRC activity" or grammatical equivalents herein is meant one of CRC's biological activities, including, but not limited to, its role in CRC.

In a preferred embodiment, the activity of the CRC protein is increased; in another preferred embodiment, the activity of the CRC protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of an CRC protein. The methods comprise adding a candidate bioactive agent, as defined above, to a cell comprising CRC proteins. Preferred cell types include almost any cell. The cells contain a recombinant nucleic acid that encodes an CRC protein. In a preferred embodiment, a library of candidate agents are tested on a plurality of cells.

In this way, bioactive agents are identified. Compounds with pharmacological activity are able to enhance or interfere with the activity of the CRC protein. The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various CRC sequences are important in CRC. Accordingly, disorders based on mutant or variant CRC genes may be determined. In one embodiment, the invention provides methods for identifying cells containing variant CRC genes comprising determining all or part of the sequence of at least one endogeneous CRC genes in a cell. As will be appreciated by those in the art, this may be done using any number of sequencing techniques. In a preferred embodiment, the invention provides methods of identifying the CRC genotype of an individual comprising determining all or part of the sequence of at least one CRC gene of the individual. This is generally done in at least one tissue of the individual, and may include the evaluation of a number of tissues or different samples of the same tissue. The method may include comparing the sequence of the sequenced CRC gene to a known CRC gene, i.e. a wild-type gene.

The sequence of all or part of the CRC gene can then be compared to the sequence of a known CRC gene to determine if any differences exist. This can be done using any number of known homology programs, such as Bestfit, etc. In a preferred embodiment, the presence of a a difference in the sequence between the CRC gene of the patient and the known CRC gene is indicative of a disease state or a propensity for a disease state, as outlined herein.

In a preferred embodiment, the CRC genes are used as probes to determine the number of copies of the CRC gene in the genome.

Thus, in one embodiment, methods of modulating CRC in cells or organisms are provided. In one embodiment, the methods comprise administering to a cell an anti-CRC antibody that reduces or eliminates the biological activity of an endogeneous CRC protein. Alternatively, the methods comprise administering to a cell or organism a recombinant nucleic acid encoding an CRC protein. As will be appreciated by those in the art, this may be accomplished in any number of ways. In a preferred embodiment, for example when the CRC sequence is down-regulated in CRC, the activity of the CRC gene is increased by increasing the amount of CRC in the cell, for example by overexpressing the endogeneous CRC or by administering a gene encoding the CRC sequence, using known gene-therapy techniques, for example. In a preferred embodiment, the gene therapy techniques include the incorporation of the exogeneous gene using enhanced homologous recombination (EHR), for example as described in PCT/US93103868, hereby incorporated by reference in its entireity. Alternatively, for example when the CRC sequence is up-regulated in CRC, the activity of the endogeneous CRC gene is decreased, for example by the administration of a CRC antisense nucleic acid.

In one embodiment, the CRC proteins of the present invention may be used to generate polyclonal and monoclonal antibodies to CRC proteins, which are useful as described herein. Similarly, the CRC proteins can be coupled, using standard technology, to affinity chromatography columns. These columns may then be used to purify CRC antibodies. In a preferred embodiment, the antibodies are generated to epitopes unique to a CRC protein; that is, the antibodies show little or no cross-reactivity to other proteins. These antibodies find use in a number of applications. For example, the CRC antibodies may be coupled to standard affinity chromatography columns and used to purify CRC proteins. The antibodies may also be used as blocking polypeptides, as outlined above, since they will specifically bind to the CRC protein.

In one embodiment, a therapeutically effective dose of an CRC is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for CRC degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the CRC proteins of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the CRC may be directly applied as a solution or spray.

The pharmaceutical compositions of the present invention comprise an CRC protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, CRC proteins are administered as therapeutic agents, and can be formulated as outlined above. Similarly, CRC genes (including both the full-length sequence, partial sequences, or regulatory sequences of the CRC coding regions) can be administered in gene therapy applications, as is known in the art. These CRC genes can include antisense applications, either as gene therapy (i.e. for incorporation into the genome) or as antisense compositions, as will be appreciated by those in the art.

In a preferred embodiment, CRC genes are administered as DNA vaccines, either single genes or combinations of CRC genes. Naked DNA vaccines are generally known in the art. Brower, Nature Biotechnology, 16:1304–1305 (1998).

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Tissue Preparation, Labeling Chips, and Fingerprints

Purify Total RNA From Tissue Using TRIzol Reagent

Estimate tissue weight. Homogenize tissue samples in 1 ml of TRIzol per 50 mg of tissue using a Polytron 3100 homogenizer. The generator/probe used depends upon the tissue size. A generator that is too large for the amount of tissue to be homogenized will cause a loss of sample and lower RNA yield. Use the 20 mm generator for tissue weighing more than 0.6 g. If the working volume is greater than 2 ml, then homogenize tissue in a 15 ml polypropylene tube (Falcon 2059). Fill tube no greater than 10 ml.

Homogenization

Before using generator, it should have been cleaned after last usage by running it through soapy H20 and rinsing thoroughly. Run through with EtOH to sterilize. Keep tissue frozen until ready. Add TRIzol directly to frozen tissue then homogenize.

Following homogenization, remove insoluble material from the homogenate by centrifugation at 7500×g for 15 min. in a Sorvall superspeed or 12,000×g for 10 min. in an Eppendorf centrifuge at 4° C. Transfer the cleared homogenate to a new tube(s). The samples may be frozen now at −60 to −70° C. (and kept for at least one month) or you may continue with the purification.

Phrase Separation

Incubate the homogenized samples for 5 minutes at room temperature. Add 0.2 ml of chloroform per 1 ml of TRIzol reagent used in the original homogenization.

Cap tubes securely and shake tubes vigorously by hand (do not vortex) for 15 seconds. Incubate samples at room temp. for 2–3 minutes. Centrifuge samples at 6500 rpm in a Sorvall superspeed for 30 min. at 4° C. (You may spin at up to 12,000×g for 10 min. but you risk breaking your tubes in the centrifuge.)

RNA Precipitation

Transfer the aqueous phase to a fresh tube. Save the organic phase if isolation of DNA or protein is desired. Add 0.5 ml of isopropyl alcohol per 1 ml of TRIzol reagent used in the original homogenization. Cap tubes securely and invert to mix. Incubate samples at room temp. for 10 minutes. Centrifuge samples at 6500 rpm in Sorvall for 20 min. at 4° C.

RNA Wash

Pour off the supernate. Wash pellet with cold 75% ethanol. Use 1 ml of 75% ethanol per 1 ml of TRIzol reagent used in the initial homogenization. Cap tubes securely and invert several times to loosen pellet. (Do not vortex). Centrifuge at <8000 rpm (<7500×g) for 5 minutes at 4° C. Pour off the wash. Carefully transfer pellet to an eppendorf tube (let it slide down the tube into the new tube and use a pipet tip to help guide it in if necessary). Depending on the volumes you are working with, you can decide what size tube(s) you want to precipitate the RNA in. When I tried leaving the RNA in the large 15ml tube, it took so long to dry (i.e. it did not dry) that I eventually had to transfer it to a smaller tube. Let pellet dry in hood. Resuspend RNA in an appropriate volume of DEPC $H_2O$. Try for 2–5 ug/ul. Take absorbance readings.

Purify Poly A+ mRNA From Total RNA or Clean up Total RNA with Qiagen's RNeasy Kit Purification of poly $A^+$ mRNA from total RNA. Heat oligotex suspension to 37° C. and mix immediately before adding to RNA. Incubate Elution Buffer at 70° C. Warm up 2×Binding Buffer at 65° C. if there is precipitate in the buffer. Mix total RNA with DEPC-treated water, 2×Binding Buffer, and Oligotex according to Table 2 on page 16 of the Oligotex Handbook. Incubate for 3 minutes at 65° C. Incubate for 10 minutes at room temperature.

Centrifuge for 2 minutes at 14,000 to 18,000 g. If centrifuge has a "soft setting," then use it. Remove supernatant without disturbing Oligotex pellet. A little bit of solution can be left behind to reduce the loss of Oligotex. Save sup until certain that satisfactory binding and elution of poly $A^+$ mRNA has occurred.

Gently resuspend in Wash Buffer OW2 and pipet onto spin column. Centrifuge the spin column at full speed (soft setting if possible) for 1 minute.

Transfer spin column to a new collection tube and gently resuspend in Wash Buffer OW2 and centrifuge as describe herein.

Transfer spin column to a new tube and elute with 20 to 100 ul of preheated (70° C.) Elution Buffer. Gently resuspend Oligotex resin by pipetting up and down. Centrifuge as above. Repeat elution with fresh elution buffer or use first eluate to keep the elution volume low.

Read absorbance, using diluted Elution Buffer as the blank.

Before proceeding with cDNA synthesis, the mRNA must be precipitated.

Some component leftover or in the Elution Buffer from the Oligotex purification procedure will inhibit downstream enzymatic reactions of the mRNA.

Ethanol Precipitation

Add 0.4 vol. of 7.5 M $NH_4OAc$ +2.5 vol. of cold 100% ethanol. Precipitate at −20° C. 1 hour to overnight (or 20–30 min. at −70° C.). Centrifuge at 14,000–16,000×g for 30 minutes at 4° C. Wash pellet with 0.5 ml of 80% ethanol (−20° C.) then centrifuge at 14,000–16,000×g for 5 minutes at room temperature. Repeat 80% ethanol wash. Dry the last bit of ethanol from the pellet in the hood. (Do not speed vacuum). Suspend pellet in DEPC $H_2O$ at 1 ug/ul concentration.

Clean Up Total RNA Using Qiagen's RNeasy Kit

Add no more than 100 ug to an RNeasy column. Adjust sample to a volume of 100 ul with RNase-free water. Add 350 ul Buffer RLT then 250 ul ethanol (100%) to the sample. Mix by pipetting (do not centrifuge) then apply sample to an RNeasy mini spin column. Centrifuge for 15 sec at >10,000rpm. If concerned about yield, re-apply flowthrough to column and centrifuge again. Transfer column to a new 2-ml collection tube. Add 500 ul Buffer RPE and centrifuge for 15 sec at >10,000 rpm. Discard flowthrough. Add 500 ul Buffer RPE and centrifuge for 15 sec at >10,000 rpm. Discard flowthrough then centrifuge for 2 min at maximum speed to dry column membrane. Transfer column to a new 1.5-ml collection tube and apply 30–50ul of RNase-free water directly onto column membrane. Centrifuge 1 min at >10,000rpm. Repeat elution. Take absorbance reading. If necessary, ethanol precipitate with ammonium acetate and 2.5× volume 100% ethanol.

Make cDNA Using Gibco's "SuperScript Choice System for cDNA Synthesis" Kit First Strand cDNA Synthesis Use 5 ug of total RNA or 1 ug of polyA+ mRNA as starting material. For total RNA, use 2 ul of SuperScript RT. For polyA+ mRNA, use 1 ul of SuperScript RT. Final volume of first strand synthesis mix is 20 ul. RNA must be in a volume no greater than 10 ul. Incubate RNA with 1 ul of 100 pmol T7–T24 oligo for 10 min at 70 C. On ice, add 7 ul of: 4 ul $5 \times 1^{st}$ Strand Buffer, 2 ul of 0.1M DTT, and 1 ul of 10 mM dNTP mix. Incubate at 37 C for 2 min then add SuperScript RT Incubate at 37 C for 1 hour.

Second Strand Synthesis

Place $1^{st}$ strand reactions on ice.

Add:

91 ul DEPC H20

30 ul $5 \times 2^{nd}$ Strand Buffer 30 ul 10 mM dNTP mix 1 ul 10 U/ul *E.coli* DNA Ligase 4 ul 10 U/ul *E.coli* DNA Polymerase 1 ul 2U/ul RNase H Make the above into a mix if there are more than 2 samples. Mix and incubate 2 hours at 16 C. Add 2 ul T4 DNA Polymerase. Incubate 5 min at 16 C. Add 10 ul of 0.5M EDTA Clean Up cDNA Phenol:Chloroform:Isoamyl Alcohol (25:24:1) purification using Phase-Lock gel tubes:

Centrifuge PLG tubes for 30 sec at maximum speed. Transfer cDNA mix to PLG tube. Add equal volume of phenol:chloroform:isamyl alcohol and shake vigorously (do not vortex). Centrifuge 5 minutes at maximum speed. Transfer top aqueous solution to a new tube. Ethanol precipitate: add 7.5×5M NH4Oac and 2.5×volume of 100% ethanol. Centrifuge immediately at room temp. for 20 min, maximum speed. Remove sup then wash pellet 2× with cold 80% ethanol. Remove as much ethanol wash as possible then let pellet air dry. Resuspend pellet in 3ul RNase-free water.

In vitro Transcription (IVI) and Labeling with Biotin

Pipet 1.5 ul of cDNA into a thin-wall PCR tube.

Make NTP Labeling Mix:

| Combine at room temperature: | | |
|---|---|---|
| | 2 ul | T7 10 × ATP (75 mM) (Ambion) |
| | 2 ul | T7 10 × GTP (75 mM) (Ambion) |
| | 1.5 ul | T7 10 × CTP (75 mM) (Ambion) |
| | 1.5 ul | T7 10 × UTP (75 mM) (Ambion) |
| | 3.75 ul | 10 mM Bio-11-UTP (Boehringer-Mannheim/Roche or Enzo) |
| | 3.75 ul | 10 mM Bio-16-CTP (Enzo) |
| | 2 ul | 10 × T7 transcription buffer (Ambion) |
| | 2 ul | 10 × T7 enzyme mix (Ambion) |

Final volume of total reaction is 20 ul. Incubate 6 hours at 37 C in a PCR machine.

RNeasy Clean-up of IVT Product

Follow previous instructions for RNeasy columns or refer to Qiagen's RNeasy protocol handbook.

cRNA will most likely need to be ethanol precipitated. Resuspend in a volume compatible with the fragmentation step.

Fragmentation 15 ug of labeled RNA is usually fragmented. Try to minimize the fragmentation reaction volume; a 10 ul volume is recommended but 20 ul is all right. Do not go higher than 20 ul because the magnesium in the fragmentation buffer contributes to precipitation in the hybridization buffer. Fragment RNA by incubation at 94 C for 35 minutes in 1×Fragmentation buffer.

5×Fragmentation Buffer:

200 mM Tris-acetate, pH 8.1

500 mM KOAc 150 mM MgOAc

The labeled RNA transcript can be analyzed before and after fragmentation. Samples can be heated to 65 C for 15 minutes and electrophoresed on 1% agarose/TBE gels to get an approximate idea of the transcript size range Hybridization 200 ul (10 ug cRNA) of a hybridization mix is put on the chip. If multiple hybridizations are to be done (such as cycling through a 5 chip set), then it is recommended that an initial hybridization mix of 300 ul or more be made.

Hybrization Mix: fragment labeled RNA (50 ng/ul final conc.)

50 pM 948-b control oligo 1.5 pM BioB 5 pM BioC 25 pM BioD 100 pM CRE 0.1 mg/ml herring sperm DNA 0.5 mg/ml acetylated BSA to 300 ul with 1×MES hyb. buffer The instruction manuals for the products used herein are incorporated herein in their entirety.

Labeling Protocol Provided Herein

Hybridization reaction:
Start with non-biotinylated IVT (purified by RNeasy columns)
(see example 1 for steps from tissue to IVT)

| | |
|---|---|
| IVT antisense RNA; 4 μg: | μl |
| Random Hexamers (1 μg/μl): | 4 μl |
| H₂O: | μl |
| | 14 μl |

Incubate 70° C., 10 min. Put on ice.
Reverse Transcription:

| | |
|---|---|
| 5 × First Strand (BRL) buffer: | 6 μl |
| 0.1 M DTT: | 3 μl |
| 50 × dNTP mix: | 0.6 μl |
| H2O: | 2.4 μl |
| Cy3 or Cy5 dUTP (1 mM): | 3 μl |
| SS RT II (BRL): | 1 μl |
| | 16 μl |

Add to hybridization reaction.
Incubate 30 min., 42° C.
Add 1 p, SSII and let go for another hour.
Put on ice.

50×dNTP mix (25 mM of cold dATP, dCTP, and dGTP, 10 mM of dTTP: 25 μl each of 100 mM dATP, dCTP, and dGTP; 10 μl of 100 mM dTTP to 15 μl H2O. dNTPs from Pharmacia)

RNA Degradation:

| | |
|---|---|
| - Add 1.5 μl 1 M NaOH/2 mM EDTA, incubate at 65° C., 10 min. | 86 μl H₂O<br>10 μl 10 N NaOH<br>4 μl 50 mM EDTA |

U-Con 30

500 μl TE/sample spin at 7000 g for 10 min, save flow through for purification

Qiagen Purification:

suspend u-con recovered material in 500 μl buffer PB proceed w/normal Qiagen protocol DNAse Digest:

Add 1 μl of 1/100 dil of DNAse/30 μl Rx and incubate at 37° C. for 15 min.

5 min 95° C. to denature enzyme

Sample Preparation:

Add:

Cot-1 DNA: 10 μl

50×dNTPs: 1 μl

20×SSC: 2.3 μl

Na pyro phosphate: 7.5 μl 10 mg/ml Herring sperm DNA 1 μl of ¹/₁₀ dilution 21.8 final vol.

Dry down in speed vac.
Resuspend in 15 μl H₂P.
Add 0.38 μl 10% SDS.
Heat 95° C., 2 min.
Slow cool at room temp. for 20 min.
Put on slide and hybridize overnight at 64° C.

Washing After the Hybridization:

3×SSC/0.03% SDS: 2 min. 37.5 mls 20×SSC+0.75 mls 10% SDS in 250 mls H₂O

1×SSC: 5 mi. 12.5 mls 20×SSC in 250 mls H₂O 0.2×SSC: 5 min. 2.5 mls 20×SSC in 250mls H₂O Dry slides in centrifuge, 1000 RPM, 1min.

Scan at appropiate PMT's and channels.

The results are shown in Tables 1 through 7. The lists of genes come from colorectal tumors from a variety of stages of the disease. The genes that are up regulated in the tumors (overall) were also found to be expressed at a limited amount or not at all in the body map. The body map for the colorectal project consists of ten tissues: Heart, Brain, Lung, Liver, Breast, Kidney, Prostrate, Small Intestine, Spleen, and Colon. The down regulated genes in tumors (overall) versus normal colon were not selected for their expression or lack of expression in the body map. As indicated, some of the Accession numbers include expression sequence tags (ESTs). Thus, in one embodiment herein, genes within an expression profile, also termed expression profile genes, include ESTs and are not necessarily full length. Table 1 shows 51 upregulated genes; Table 2 shows 194 upregulated genes; Tables 3 shows 1144 upregulated genes and table 4 shows 1815 upregulated genes. The genes shown in Tables 1 and 5 are particularly preferred. Table 5 shows 54 downregulated genes; Table 6 shows 558 downregulated genes; and Table 7 shows 1923 downregulated genes.

We claim:

1. A method of screening for a bioactive agent capable of binding to a protein which is differentially expressed in colorectal cancer, said method comprising combining said protein and a candidate bioactive agent, and determining the binding of said candidate agent to said protein, wherein said protein is encoded by a nucleic acid comprising SEQ ID NO. 1.

2. The method of claim 1, wherein said candidate bioactive agent is an antibody.

3. The method of claim 2, wherein said antibody is an antibody fragment selected from the group consisting of a Fab, $Fab_2$, single chain antibody and chimeric antibody.

4. The method of claim 2, wherein said antibody is capable of reducing or eliminating the biological function of said protein.

5. The method of claim 1, wherein said bioactive agent is selected from the group consisting of a protein, a peptide, an oligopeptide, a nucleic acid, a small organic molecule, a polysaccharide and a polynucleotide.

6. The method of claim 2 or 5, wherein said protein or candidate bioactive agent comprises a label.

7. The method of claim 2 or 5, wherein said protein comprises a tag polypeptide.

8. The method of claim 2 or 5, wherein said protein or candidate bioactive agent is non-diffusably bound to an insoluble support.

9. The method of claim 2, further comprising combining a competitor and said protein, either prior to or following combining said protein and said candidate bioactive agent and, alternatively, determining the binding of said competitor to said protein.

10. The method of claim 9, wherein said candidate bioactive agent and/or said competitor comprises a label.

11. The method of claim 1, wherein said candidate bioactive agent is a protein.

12. The method of claim 11, wherein said protein is a peptide.

13. The method of claim 1, wherein said candidate bioactive agent is a nucleic acid.

14. The method of claim 1, wherein said candidate bioactive agent is a small organic molecule.

15. The method of claim 1, wherein said candidate bioactive agent is a polysaccharide.

* * * * *

SEQUENCE LISTING

<160> NUMBER OF SEQ ID NOS: 2

<210> SEQ ID NO 1
<211> LENGTH: 4098
<212> TYPE: DNA
<213> ORGANISM: Homo sapiens

<400> SEQUENCE: 1

| | | | | | | |
|---|---|---|---|---|---|---|
| ggtggcctct | gtggccgtcc | aggctagcgg | cggcccgcag | gcggcgggga | gaaagactct | 60 |
| ctcacctggt | cttgcggctg | tggccaccgc | cggccagggg | tgtggagggc | gtgctgccgg | 120 |
| agacgtccgc | cgggctctgc | agttccgccg | gggtcgggc | agctatggag | ccgcggccca | 180 |
| cggcgccctc | ctccggcgcc | ccgggactgg | ccggggtcgg | ggagacgccg | tcagccgctg | 240 |
| cgctggccgc | agccagggtg | gaactgcccg | gcacggctgt | gccctcggtg | ccggaggatg | 300 |
| ctgcgcccgc | gagccgggac | ggcggcgggg | tccgcgatga | gggccccgcg | gcggccgggg | 360 |
| acgggctggg | cagacccttg | gggcccaccc | cgagccagag | ccgtttccag | gtggacctgg | 420 |
| tttccgagaa | cgccgggcgg | gccgctgctg | cggcggcggc | ggcggcggcg | gcagcggcgg | 480 |
| cggctggtgc | tggggcgggg | gccaagcaga | ccccgcgga | cggggaagcc | agcggcgaga | 540 |
| gcgagccagc | taaaggcagc | gaggaagcca | agggccgctt | ccgcgtgaac | ttcgtggacc | 600 |
| cagctgcctc | ctcgtcggct | gaagacagcc | tgtcagatgc | tgccggggtc | ggagtcgacg | 660 |
| ggcccaacgt | gagcttccag | aacggcgggg | acacggtgct | gagcgagggc | agcagcctgc | 720 |
| actccggcgg | cggcggcggc | agtgggcacc | accagcacta | ctattatgat | acccacacca | 780 |
| acacctacta | cctgcgcacc | ttcggccaca | caccatgga | cgctgtgccc | aggatcgatc | 840 |
| actaccggca | cacagccgcg | cagctgggcg | agaagctgct | ccggcctagc | ctggcggagc | 900 |
| tccacgacga | gctggaaaag | gaaccttttg | aggatgcct | tgcaaatggg | gaagaaagta | 960 |
| ctccaaccag | agatgctgtg | gtcacgtata | ctgcagaaag | taaggagtc | gtgaagtttg | 1020 |
| gctggatcaa | gggtgtatta | gtacgttgta | tgttaaacat | ttgggtgtg | atgcttttca | 1080 |
| ttagattgtc | atggattgtg | ggtcaagctg | gaataggtct | atcagtcctt | gtaataatga | 1140 |
| tggccactgt | tgtgacaact | atcacaggat | tgtctacttc | agcaatagca | actaatggat | 1200 |
| ttgtaagagg | aggaggagca | tattatttaa | tatctagaag | tctagggcca | gaatttggtg | 1260 |
| gtgcaattgg | tctaatcttc | gcctttgcca | acgctgttgc | agttgctatg | tatgtggttg | 1320 |
| gatttgcaga | aaccgtggtg | gagttgctta | aggaacattc | catacttatg | atagatgaaa | 1380 |
| tcaatgatat | ccgaattatt | ggagccatta | cagtcgtgat | tcttttaggt | atctcagtag | 1440 |
| ctggaatgga | gtgggaagca | aaagctcaga | ttgttctttt | ggtgatccta | cttcttgcta | 1500 |
| ttggtgattt | cgtcatagga | acatttatcc | cactggagag | caagaagcca | aaagggtttt | 1560 |
| ttggttataa | atctgaaata | tttaatgaga | actttgggcc | cgattttcga | gaggaagaga | 1620 |
| ctttcttttc | tgtatttgcc | atctttttc | ctgctgcaac | tggtattctg | gctggagcaa | 1680 |
| atatctcagg | tgatcttgca | gatcctcagt | cagccatacc | caaaggaaca | ctcctagcca | 1740 |
| ttttaattac | tacattggtt | tacgtaggaa | ttgcagtatc | tgtaggttct | tgtgttgttc | 1800 |
| gagatgccac | tggaaacgtt | aatgacacta | tcgtaacaga | gctaacaaac | tgtacttctg | 1860 |
| cagcctgcaa | attaaacttt | gatttttcat | cttgtgaaag | cagtccttgt | tcctatggcc | 1920 |
| taatgaacaa | cttccaggta | atgagtatgg | tgtcaggatt | tacaccacta | atttctgcag | 1980 |
| gtatattttc | agccactctt | tcttcagcat | tagcatccct | agtgagtgct | cccaaaatat | 2040 |

```
ttcaggctct atgtaaggac aacatctacc cagctttcca gatgtttgct aaaggttatg    2100
ggaaaaataa tgaacctctt cgtggctaca tcttaacatt cttaattgca cttggattca    2160
tcttaattgc tgaactgaat gttattgcac caattatctc aaacttcttc cttgcatcat    2220
atgcattgat caatttttca gtattccatg catcacttgc aaaatctcca ggatggcgtc    2280
ctgcattcaa atactacaac atgtggatat cacttcttgg agcaattctt tgttgcatag    2340
taatgttcgt cattaactgg tgggctgcat tgctaacata tgtgatagtc cttgggctgt    2400
atatttatgt tacctacaaa aaaccagatg tgaattgggg atcctctaca caagccctga    2460
cttacctgaa tgcactgcag cattcaattc gtctttctgg agtggaagac cacgtgaaaa    2520
actttaggcc acagtgtctt gttatgacag gtgctccaaa ctcacgtcca gctttacttc    2580
atcttgttca tgatttcaca aaaaatgttg gtttgatgat ctgtggccat gtacatatgg    2640
gtcctcgaag acaagccatg aaagagatgt ccatcgatca agccaaatat cagcgatggc    2700
ttattaagaa caaaatgaag gcattttatg ctccagtaca tgcagatgac ttgagagaag    2760
gtgcacagta tttgatgcag gctgctggtc ttggtcgtat gaagccaaac acacttgtcc    2820
ttggatttaa gaaagattgg ttgcaagcag atatgaggga tgtggatatg tatataaact    2880
tatttcatga tgcttttgac atacaatatg gagtagtggt tattcgccta aaagaaggtc    2940
tggatatatc tcatcttcaa ggacaagaag aattattgtc atcacaagag aaatctcctg    3000
gcaccaagga tgtggtagta agtgtggaat atagtaaaaa gtccgattta gatacttcca    3060
aaccactcag tgaaaaacca attacacaca agttgagga agaggatggc aagactgcaa    3120
ctcaaccact gttgaaaaaa gaatccaaag gccctattgt gcctttaaat gtagctgacc    3180
aaaagcttct tgaagctagt acacagtttc agaaaaaaca aggaaagaat actattgatg    3240
tctggtggct ttttgatgat ggaggtttga ccttattgat accttacctt ctgacgacca    3300
agaaaaaatg gaaagactgt aagatcagag tattcattgg tggaaagata aacagaatag    3360
accatgaccg gagagcgatg gctactttgc ttagcaagtt ccggatagac ttttctgata    3420
tcatggttct aggagatatc aataccaaac caaagaaaga aatatatta gcttttgagg    3480 aaatcattga gccatacaga cttcatgaag atgataaaga gcaagatatt gcagataaaa    3540
tgaaagaaga tgaaccatgg cgaataacag ataatgagct tgaactttat aagaccaaga    3600
cataccggca gatcaggtta aatgagttat taaggaaca ttcaagcaca gctaatatta    3660
ttgtcatgag tctcccagtt gcacgaaaag gtgctgtgtc tagtgctctc tacatggcat    3720
ggttagaagc tctatctaag gacctaccac caatcctcct agttcgtggg aatcatcaga    3780
gtgtccttac cttctattca taaatgttct atacagtgga cagccctcca gaatggtact    3840
tcagtgccta gtgtagtaac ctgaaatctt caatgacaca ttaacatcac aatggcgaat    3900
ggtgactttt ctttcacgat ttcattaatt tgaaagcaca caggaaagct tgctccattg    3960
ataacgtgta tggagacttc ggttttagtc aattccatat ctcaatctta atggtgattc    4020
ttctctgttg aactgaagtt tgtgagagta gttttccttt gctacttgaa tagcaataaa    4080
agcgtgttaa cttttttgg                                                4098
```

<210> SEQ ID NO 2
<211> LENGTH: 1212
<212> TYPE: PRT
<213> ORGANISM: Homo sapiens

<400> SEQUENCE: 2

-continued

```
Met Glu Pro Arg Pro Thr Ala Pro Ser Ser Gly Ala Pro Gly Leu Ala
 1               5                  10                  15

Gly Val Gly Glu Thr Pro Ser Ala Ala Leu Ala Ala Ala Arg Val
            20                  25                  30

Glu Leu Pro Gly Thr Ala Val Pro Ser Val Pro Glu Asp Ala Ala Pro
            35                  40                  45

Ala Ser Arg Asp Gly Gly Val Arg Asp Gly Pro Ala Ala Ala
        50                  55                  60

Gly Asp Gly Leu Gly Arg Pro Leu Gly Pro Thr Pro Ser Gln Ser Arg
 65                  70                  75                  80

Phe Gln Val Asp Leu Val Ser Glu Asn Ala Gly Arg Ala Ala Ala
                85                  90                  95

Ala Ala Ala Ala Ala Ala Ala Ala Gly Ala Gly Ala Gly
            100                 105                 110

Ala Lys Gln Thr Pro Ala Asp Gly Glu Ala Ser Gly Glu Ser Glu Pro
            115                 120                 125

Ala Lys Gly Ser Glu Glu Ala Lys Gly Arg Phe Arg Val Asn Phe Val
            130                 135                 140

Asp Pro Ala Ala Ser Ser Ser Ala Glu Asp Ser Leu Ser Asp Ala Ala
145                 150                 155                 160

Gly Val Gly Val Asp Gly Pro Asn Val Ser Phe Gln Asn Gly Gly Asp
                165                 170                 175

Thr Val Leu Ser Glu Gly Ser Ser Leu His Ser Gly Gly Gly Gly
            180                 185                 190

Ser Gly His His Gln His Tyr Tyr Tyr Asp Thr His Thr Asn Thr Tyr
            195                 200                 205

Tyr Leu Arg Thr Phe Gly His Asn Thr Met Asp Ala Val Pro Arg Ile
    210                 215                 220

Asp His Tyr Arg His Thr Ala Ala Gln Leu Gly Glu Lys Leu Leu Arg
225                 230                 235                 240

Pro Ser Leu Ala Glu Leu His Asp Glu Leu Glu Lys Glu Pro Phe Glu
                245                 250                 255

Asp Gly Phe Ala Asn Gly Glu Glu Ser Thr Pro Thr Arg Asp Ala Val
            260                 265                 270

Val Thr Tyr Thr Ala Glu Ser Lys Gly Val Val Lys Phe Gly Trp Ile
            275                 280                 285

Lys Gly Val Leu Val Arg Cys Met Leu Asn Ile Trp Gly Val Met Leu
            290                 295                 300

Phe Ile Arg Leu Ser Trp Ile Val Gly Gln Ala Gly Ile Gly Leu Ser
305                 310                 315                 320

Val Leu Val Ile Met Met Ala Thr Val Thr Thr Ile Thr Gly Leu
                325                 330                 335

Ser Thr Ser Ala Ile Ala Thr Asn Gly Phe Val Arg Gly Gly Gly Ala
            340                 345                 350

Tyr Tyr Leu Ile Ser Arg Ser Leu Gly Pro Glu Phe Gly Gly Ala Ile
            355                 360                 365

Gly Leu Ile Phe Ala Phe Ala Asn Ala Val Ala Val Ala Met Tyr Val
    370                 375                 380

Val Gly Phe Ala Glu Thr Val Val Glu Leu Leu Lys Glu His Ser Ile
385                 390                 395                 400

Leu Met Ile Asp Glu Ile Asn Asp Ile Arg Ile Ile Gly Ala Ile Thr
                405                 410                 415

Val Val Ile Leu Leu Gly Ile Ser Val Ala Gly Met Glu Trp Glu Ala
```

-continued

```
                420                 425                 430
Lys Ala Gln Ile Val Leu Leu Val Ile Leu Leu Ala Ile Gly Asp
            435                 440                 445
Phe Val Ile Gly Thr Phe Ile Pro Leu Glu Ser Lys Lys Pro Lys Gly
450                 455                 460
Phe Phe Gly Tyr Lys Ser Glu Ile Phe Asn Glu Asn Phe Gly Pro Asp
465                 470                 475                 480
Phe Arg Glu Glu Thr Phe Ser Val Phe Ala Ile Phe Phe Pro
            485                 490                 495
Ala Ala Thr Gly Ile Leu Ala Gly Ala Asn Ile Ser Gly Asp Leu Ala
            500                 505                 510
Asp Pro Gln Ser Ala Ile Pro Lys Gly Thr Leu Leu Ala Ile Leu Ile
            515                 520                 525
Thr Thr Leu Val Tyr Val Gly Ile Ala Val Ser Val Gly Ser Cys Val
530                 535                 540
Val Arg Asp Ala Thr Gly Asn Val Asn Asp Thr Ile Val Thr Glu Leu
545                 550                 555                 560
Thr Asn Cys Thr Ser Ala Ala Cys Lys Leu Asn Phe Asp Phe Ser Ser
            565                 570                 575
Cys Glu Ser Ser Pro Cys Ser Tyr Gly Leu Met Asn Asn Phe Gln Val
            580                 585                 590
Met Ser Met Val Ser Gly Phe Thr Pro Leu Ile Ser Ala Gly Ile Phe
            595                 600                 605
Ser Ala Thr Leu Ser Ser Ala Leu Ala Ser Leu Val Ser Ala Pro Lys
            610                 615                 620
Ile Phe Gln Ala Leu Cys Lys Asp Asn Ile Tyr Pro Ala Phe Gln Met
625                 630                 635                 640
Phe Ala Lys Gly Tyr Gly Lys Asn Asn Glu Pro Leu Arg Gly Tyr Ile
            645                 650                 655
Leu Thr Phe Leu Ile Ala Leu Gly Phe Ile Leu Ile Ala Glu Leu Asn
            660                 665                 670
Val Ile Ala Pro Ile Ile Ser Asn Phe Phe Leu Ala Ser Tyr Ala Leu
            675                 680                 685
Ile Asn Phe Ser Val Phe His Ala Ser Leu Ala Lys Ser Pro Gly Trp
            690                 695                 700
Arg Pro Ala Phe Lys Tyr Tyr Asn Met Trp Ile Ser Leu Leu Gly Ala
705                 710                 715                 720
Ile Leu Cys Cys Ile Val Met Phe Val Ile Asn Trp Trp Ala Ala Leu
                    725                 730                 735
Leu Thr Tyr Val Ile Val Leu Gly Leu Tyr Ile Tyr Val Thr Tyr Lys
            740                 745                 750
Lys Pro Asp Val Asn Trp Gly Ser Ser Thr Gln Ala Leu Thr Tyr Leu
            755                 760                 765
Asn Ala Leu Gln His Ser Ile Arg Leu Ser Gly Val Glu Asp His Val
            770                 775                 780
Lys Asn Phe Arg Pro Gln Cys Leu Val Met Thr Gly Ala Pro Asn Ser
785                 790                 795                 800
Arg Pro Ala Leu Leu His Leu Val His Asp Phe Thr Lys Asn Val Gly
            805                 810                 815
Leu Met Ile Cys Gly His Val His Met Gly Pro Arg Arg Gln Ala Met
            820                 825                 830
Lys Glu Met Ser Ile Asp Gln Ala Lys Tyr Gln Arg Trp Leu Ile Lys
            835                 840                 845
```

-continued

```
Asn Lys Met Lys Ala Phe Tyr Ala Pro Val His Ala Asp Asp Leu Arg
    850                 855                 860
Glu Gly Ala Gln Tyr Leu Met Gln Ala Ala Gly Leu Gly Arg Met Lys
865                 870                 875                 880
Pro Asn Thr Leu Val Leu Gly Phe Lys Lys Asp Trp Leu Gln Ala Asp
                885                 890                 895
Met Arg Asp Val Asp Met Tyr Ile Asn Leu Phe His Asp Ala Phe Asp
            900                 905                 910
Ile Gln Tyr Gly Val Val Val Ile Arg Leu Lys Glu Gly Leu Asp Ile
        915                 920                 925
Ser His Leu Gln Gly Gln Glu Glu Leu Leu Ser Ser Gln Glu Lys Ser
    930                 935                 940
Pro Gly Thr Lys Asp Val Val Ser Val Glu Tyr Ser Lys Lys Ser
945                 950                 955                 960
Asp Leu Asp Thr Ser Lys Pro Leu Ser Glu Lys Pro Ile Thr His Lys
                965                 970                 975
Val Glu Glu Glu Asp Gly Lys Thr Ala Thr Gln Pro Leu Leu Lys Lys
            980                 985                 990
Glu Ser Lys Gly Pro Ile Val Pro Leu Asn Val Ala Asp Gln Lys Leu
        995                 1000                1005
Leu Glu Ala Ser Thr Gln Phe Gln Lys Lys Gln Gly Lys Asn Thr Ile
    1010                1015                1020
Asp Val Trp Trp Leu Phe Asp Asp Gly Gly Leu Thr Leu Leu Ile Pro
1025                1030                1035                1040
Tyr Leu Leu Thr Thr Lys Lys Lys Trp Lys Asp Cys Lys Ile Arg Val
                1045                1050                1055
Phe Ile Gly Gly Lys Ile Asn Arg Ile Asp His Asp Arg Arg Ala Met
            1060                1065                1070
Ala Thr Leu Leu Ser Lys Phe Arg Ile Asp Phe Ser Asp Ile Met Val
        1075                1080                1085
Leu Gly Asp Ile Asn Thr Lys Pro Lys Lys Glu Asn Ile Ile Ala Phe
    1090                1095                1100
Glu Glu Ile Ile Glu Pro Tyr Arg Leu His Glu Asp Asp Lys Glu Gln
1105                1110                1115                1120
Asp Ile Ala Asp Lys Met Lys Glu Asp Glu Pro Trp Arg Ile Thr Asp
                1125                1130                1135
Asn Glu Leu Glu Leu Tyr Lys Thr Lys Thr Tyr Arg Gln Ile Arg Leu
            1140                1145                1150
Asn Glu Leu Leu Lys Glu His Ser Ser Thr Ala Asn Ile Ile Val Met
        1155                1160                1165
Ser Leu Pro Val Ala Arg Lys Gly Ala Val Ser Ser Ala Leu Tyr Met
    1170                1175                1180
Ala Trp Leu Glu Ala Leu Ser Lys Asp Leu Pro Pro Ile Leu Leu Val
1185                1190                1195                1200
Arg Gly Asn His Gln Ser Val Leu Thr Phe Tyr Ser
                1205                1210
```